United States Patent
Derrieu

(10) Patent No.: US 9,421,232 B2
(45) Date of Patent: Aug. 23, 2016

(54) METHOD OF PREPARATION OF COMPOSITIONS COMPRISING DEHYDRATED MICRO-ORGANISMS

(71) Applicant: VIRBAC SA, Carros (FR)

(72) Inventor: Guy Derrieu, Cagnes sur Mer (FR)

(73) Assignee: VIRBAC SA, Carros (FR)

( * ) Notice: Subject to any disclaimer, the term of this patent is extended or adjusted under 35 U.S.C. 154(b) by 0 days.

(21) Appl. No.: 14/991,773

(22) Filed: Jan. 8, 2016

(65) Prior Publication Data

US 2016/0120921 A1    May 5, 2016

Related U.S. Application Data

(62) Division of application No. 11/815,703, filed as application No. PCT/FR2006/000258 on Feb. 6, 2006, now Pat. No. 9,259,448.

(30) Foreign Application Priority Data

Feb. 7, 2005   (FR) ...................................... 05 01232

(51) Int. Cl.
| | |
|---|---|
| C12N 1/04 | (2006.01) |
| A61K 35/747 | (2015.01) |
| A61K 35/744 | (2015.01) |
| A61K 9/19 | (2006.01) |
| A61K 9/20 | (2006.01) |
| A23L 1/30 | (2006.01) |
| A23L 1/302 | (2006.01) |
| A23L 1/304 | (2006.01) |
| A23L 1/305 | (2006.01) |
| A23L 1/00 | (2006.01) |

(52) U.S. Cl.
CPC ............. *A61K 35/747* (2013.01); *A23L 1/0026* (2013.01); *A23L 1/30* (2013.01); *A23L 1/302* (2013.01); *A23L 1/304* (2013.01); *A23L 1/3014* (2013.01); *A23L 1/3051* (2013.01); *A61K 9/19* (2013.01); *A61K 9/20* (2013.01); *A61K 35/744* (2013.01); *A23Y 2220/67* (2013.01); *A23Y 2240/00* (2013.01)

(58) Field of Classification Search
None
See application file for complete search history.

(56) References Cited

U.S. PATENT DOCUMENTS

| | | | |
|---|---|---|---|
| 5,932,782 A | 8/1999 | Bidney | |
| 7,037,708 B1 | 5/2006 | Runge et al. | |
| 2003/0109025 A1 | 6/2003 | Durand et al. | |
| 2004/0175389 A1 | 9/2004 | Porubcan | |

FOREIGN PATENT DOCUMENTS

| | | |
|---|---|---|
| EP | 0486234 A2 | 5/1992 |
| FR | 2806417 A1 | 9/2001 |

OTHER PUBLICATIONS

International Search Report of PCT/FR2006/000258, date of mailing Aug. 3, 2006; in English (2 pages).

Mississippi Beaches Closure History 2000-2004, Mississippi Department of Environmental Quality, Sep. 28, 2004, http://www.usm.edu/gcrl/msbeach/closehis_2000-2004.htm accessed Feb. 3, 2011; (5 pages).

Soil Particle Size, Michigan Environmental Education Curriculum, http://techalive.mtu.edu/meec/module06/SoiClassification.htm, accessed Feb. 3, 2011; (1 page).

C. Laroche et al., "Water activity affects heat resistance of microorganisms in food powders", Int'l J. of Food Microbiol., vol. 97, pp. 307-315 (Jan. 1, 2005).

Xavier Gautier, "Comparaison de deux techniques de séchage en granulation humide" ("Comparison of two drying techniques in wet granulation"), Ph.D. Pharmacy Thesis, Nancy-University, France (Sep. 16, 2003), available at http://docnum.univ-lorraine.fr/public/SCDPHA_T_2003_GAUTHIER_XAVIER.pdf, with partial English machine-translation (sections 1.1.2. and 1.1.2.1) (7 pages).

*Primary Examiner* — Irene Marx
(74) *Attorney, Agent, or Firm* — Westerman, Hattori, Daniels & Adrian, LLP

(57) ABSTRACT

The invention relates to a composition comprising revivable dehydrated micro-organisms. The invention is characterized in that it further comprises particles at least 50% of which have a mean diameter greater than 250 μm. The invention is applicable, in particular, to human or veterinary pharmaceuticals, to dietetics or to food products.

5 Claims, No Drawings

METHOD OF PREPARATION OF COMPOSITIONS COMPRISING DEHYDRATED MICRO-ORGANISMS

CROSS-REFERENCE TO RELATED APPLICATIONS

This application is a divisional of U.S. application Ser. No. 11/815,703 filed Feb. 13, 2008, which is a U.S. national stage of International application No. PCT/FR2006/000258 filed Feb. 6, 2006, each of which claims priority of French application No. 05 01232 filed Feb. 7, 2005, the entire contents of each of which being hereby incorporated by reference.

FIELD OF THE INVENTION

This invention relates to compositions comprising revivable dehydrated micro-organisms, methods of preparing such compositions, and their uses as food intake, in particular dietetic, or as a drug.

BACKGROUND OF THE INVENTION

The intestinal flora of man and animals, in particular warm-blooded animals, contains numerous species of micro-organisms. In particular, these are bacteria the presence of which is essential, not only to digestion, but also, and more generally speaking, to health.

Therefore, numerous food products or drugs have been developed with a view to providing micro-organisms capable of reconstituting the intestinal flora of man and animals.

In manufacturing such food products or such drugs, the micro-organisms are generally dehydrated in advance. They are further associated with compounds, said compounds advantageously having prebiotic properties, i.e., being capable of stimulating the growth of micro-organisms.

However, the dehydrated micro-organisms of these food products are subjected to stresses. Furthermore, these are stresses which are not necessarily due to the environment. Chemical stresses such as acidity, or enzymatic stresses may be cited, for example.

The effect of these stresses is to affect the viability of the dehydrated micro-organisms with the result being that, for all practical purposes, it is not possible to guarantee the presence of a substantial quantity of revivable micro-organisms in these food products, and this is so even when the storage life of said products is short.

Of course, it has been sought to develop compositions containing revivable dehydrated micro-organisms in which said micro-organisms are protected from the physicochemical stresses to which they are normally subjected.

These compositions aim to protect the micro-organisms by coating them with a protective substance. They are disclosed, in particular, in the documents published under the numbers FR 2 806 417, FR 2 748 752 and US 2004/0175389. In the document FR 2 806 417, micro-organisms are coated with a protective hydrophobic substance. In addition, in the patent FR 2 748 452, bacteria are coated with polymers. Finally, in the document US 2004/0175389, bacteria are coated with an alginic acid gel.

Nevertheless, the coating of dehydrated bacteria is an operation which is stressful in itself, and which consequently ends up destroying a substantial quantity of the bacteria present in the compositions obtained. Furthermore, coating is a relatively complex and random operation from product to product.

SUMMARY OF THE INVENTION

In light of the foregoing, one problem the invention proposes to resolve is to produce a composition comprising revivable dehydrated micro-organisms, as well as a method for preparing such a composition, which introduces a certain stability of the micro-organisms over time.

The first object of the solution of the invention to this posed problem is a composition containing revivable dehydrated micro-organisms, characterised in that it further comprises particles 50% of which have a mean diameter greater than 250 µm.

The second object is a method for preparing a food or medicinal composition, characterized in that it comprises the following steps of:
dehydrating revivable micro-organisms; and
mixing the dehydrated micro-organisms with particles at least 50% of which have a mean diameter greater than 250 µm.

Finally, the third object is the use of a composition such as the one above, as a food intake or drug for human or veterinary use.

Surprisingly, when a composition includes both dehydrated micro-organisms and particles at least 50% of which have a mean diameter greater than 250 µm, a substantial quantity of dehydrated micro-organisms, in actual practice more than 20%, remains revivable for a minimum of 18 months.

MODE(S) FOR CARRYING OUT THE INVENTION

The invention will be better understood upon reading the following non-limiting description.

The composition according to the invention comprises micro-organisms and particles.

The micro-organisms of the composition according to the invention are microscopic-sized eukaryotic or prokaryotic unicellular organisms. These are preferably bacteria or yeasts, and more preferably bacteria or yeasts having probiotic properties i.e., useful to the organism of the human body or to the animal organism.

Among the bacteria capable of entering into the compositions according to the invention, bacteria of the family Lactobacillaceae, Bifidobacteriaceae, Streptococcaceae, Enterococcaceae or Bacillaceae will advantageously be chosen. The following species can be cited as non-limiting examples of bacteria of the family Lactobacillaceae: *Lactobacillus acidophilus, Lactobacillus amylovorus, Lactobacillus brevis, Lactobacillus bulgaricus, Lactobacillus casei, Lactobacillus casei rhamnosus, Lactobacillus delbrueckii, Lactobacillus farciminis, Lactobacillus fermentum, Lactobacillus gasseri, Lactobacillus helveticus, Lactobacillus johnsonii, Lactobacillus lactis, Lactobacillus paracasei, Lactobacillus plantarum, Lactobacillus pentosaceus, Lactobacillus reuteri, Lactobacillus rhamnosus, Lactobacillus salivarius* and *Pediococcus acidilactici*. The following species can be cited as non-limiting examples of bacteria of the family Bifidobacteriaceae: *Bifidobacterium animalis, Bifidobacterium bifidum, Bifidobacterium breve, Bifidobacterium infantis, Bifidobacterium lactis, Bifidobacterium longum* and *Bifidobacterium pseudolongum*.

The following species can be cited as non-limiting examples of bacteria of the family Streptococcaceae: *Streptococcus infantarius, Streptococcus thermophilus, Streptococcus salivarius*, and *Lactococcus lactis*. The species *Enterococcus faecium* can be cited as a non-limiting example of bacteria of the family Enterococcaceae. The following species can be cited as non-limiting examples of bacteria of the family Bacillaceae: *Bacillus cereus, Bacillus licheniformis, Bacillus subtilis*.

Among the yeasts capable of entering into the compositions of the invention, yeasts of the family Saccharomycetaceae will advantageously be chosen. The genera *Saccha-*

*romyces*, such as *Saccharomyces boulardii* and *Saccharomyces cerevisiae* and *Kluyveromyces* can be cited.

The micro-organisms according to the invention are dehydrated. The size of said micro-organisms, after dehydration, is generally less than 50 µm. They are obtained via conventional methods such as grinding after lyophilization, and via spray drying or air-fluidized bed drying of relatively concentrated and relatively pure micro-organism biomasses.

Furthermore, the micro-organisms according to the invention are revivable. Correspondingly, they have the capacity to resume the activity of life after a period of anhydrobiosis.

The particles of the composition according to the invention are capable of including any constituent, alone or in a mixture, which is used in manufacturing or preparing a food or medicinal composition. In particular, these are vitamins, trace elements, minerals and the salts thereof, carriers such as sugars or amino acids or vegetable flours, alone or in a mixture, introducing various properties into said composition, e.g., physical properties, such as its solubilisation in an aqueous medium or effervescence in the presence of such a medium, therapeutic properties, assistance in re-growth, a nutritional supplement or palatability. These can also be pharmaceutical active principles, e.g., such as antibiotics, anti-inflammatories, anti-parasitic agents, antacids, analgesics or tranquilizers. The particles are generally substantially devoid of micro-organisms.

Non-limiting examples of vitamins that can be cited include vitamin A, vitamin B1, vitamin B2, vitamin B3, vitamin B4, vitamin B5, vitamin B6, vitamin B8, vitamin B9, vitamin B12, vitamin BT, vitamin Bx, vitamin C, vitamin D, vitamin D2, vitamin D3, vitamin E, vitamin F, vitamin G, vitamin H, vitamin K, vitamin K3, vitamin M, vitamin P, vitamin P4 and vitamin PP. Non-limiting examples of trace elements that can be cited include calcium, cobalt, copper, iron, fluorine, iodine, magnesium, manganese, selenium and zinc. A non-limiting example of a source of minerals that can be cited includes, in particular, calcium chloride, potassium chloride, copper gluconate, sodium fluoride, potassium iodide, manganese sulphate, magnesium stearate, zinc sulphate and ferrous succinate. A non-limiting example of a carrier that can be cited includes carrier sugars and agents such as fructans, in particular inulin, fructo-oligosaccharides (FOS), galacto-oligosaccharides (GOS), or trans-galacto-oligosaccharides (TOS), xylooligosaccharides (XOS), certain maltodextrins, polydextroses, lactulose, amino acids and food fibbers. The vegetable flours, for example, are residues of oleaginous seeds or fruits, from which the oil was extracted.

In addition, the particles of the composition according to the invention advantageously contain effervescent agents consisting of a mixture of at least one acid and one alkaline agent. Non-limiting examples of acids that can be cited include tartaric acid, citric acid, maleic acid, fumaric acid, malic acid, adipic acid, succinic acid, lactic acid, glycolic acid, alpha-hydroxy acids, ascorbic acid and the amino acids, as well as the salts and derivatives of these acids. Non-limiting examples of alkaline agents that can be cited include potassium bicarbonate, sodium bicarbonate, potassium carbonate, sodium carbonate, calcium carbonate, ammonium carbonate, L-lysine carbonate, arginine carbonate, glycine sodium carbonate or sodium amino acid carbonates.

The aforesaid constituents are generally in a solid form. The particles are dried, at least at their surface, and are quite often spherical, ovoid or elongated in shape. Their surface is evenly or unevenly smooth or rough.

According to the invention, at least 50% of the particles have a mean diameter greater than 250 µm and less than 2,000 µm, preferably 1,000 µm. They are distributed within a particle-size range almost exclusively between 20 and 2,000 µm, and preferably between 50 and 1,000 µm.

The particles can be obtained via granulation and, consequently, are in the form of granules. Granulation such as this can be carried out via mixing in a wet medium, and includes drying and then sizing steps. It can also be carried out in a fluidized-air bed or on devices known in the prior art, which combine a set of operations resulting in the desired particles, via compacting, via granulation or via coating. In this final alternative, the particles are coated.

The composition according to the invention can further contain food additives such as preservatives, anti-oxidants, supports, acidifiers, acidity regulators, anti-caking agents, anti-foaming agents, emulsifiers, flavour enhancers, foaming agents, gel-forming substances, coating agents, humectants, modified starches, sequestering agents, stabilisers, thickeners and water retention agents.

The composition according to the invention, for example, is the result of a simple mechanical mixing of dehydrated micro-organisms and particles as described above. In actual practice, it preferably comprises between 1 and 80% w/w (weight of the total weight of the composition) dehydrated micro-organisms, and between 20 and 99% w/w particles and, more preferably, between 10 and 40% w/w dehydrated micro-organisms and between 60 and 90% w/w particles.

In addition, the composition according to the invention is dry, i.e., unsaturated or slightly saturated with a liquid and, in particular, with water. It preferably has a water activity lower than 0.3 and, more preferably, a water activity lower than 0.2.

The composition according to the invention is in any pharmaceutical form normally used for oral administration. Thus it can be in powder form and placed in pouches, jars or bags, said composition possibly being effervescent, and intended to be dissolved in water. It can also be in the form of capsules or gelatine capsules, possibly enteric, with a hard or soft casing, or else, for example, in the form of tablets or prolonged-release, coated or uncoated, buccal, sublingual or effervescent granules, for example.

In actual practice, the compositions according to the invention can be kept moisture-free and at room temperature for a relatively long time period. Surprisingly, the quantity of revivable micro-organisms in these compositions at the end of this time period is well above the quantity of micro-organisms that it would have been possible to obtain in compositions of the prior art, kept under the same conditions. Thus, if it is considered that at a time=0, corresponding to its packaging, a composition according to the invention contains 100% revivable micro-organisms, then, after 18 months, a composition such as this, if kept moisture-free and at room temperature, will contain at least approximately 20% revivable micro-organisms, after counting the number of micro-organisms (by counting the colonies obtained after inoculation into or onto an appropriate culture medium). This appears to be significant with regard to the compositions of the prior art.

In a preferred embodiment according to the invention, the composition is soluble or dispersible in an aqueous medium. It can also be effervescent. Therefore, when it is added to water, e.g., intended for feeding large animals such as horses or cattle, it dissolves or disperses. Effervescence facilitates the dissolution or dispersion of the composition in water and its diffusion within this aqueous medium. The revivable micro-organisms present in the composition are rehydrated. Rehydration is a fast step lasting a few minutes. At the end of these few minutes, large animals, absorbing the water in which the composition is dissolved or dispersed, ingest rehydrated micro-organisms as well as ingredients useful to their body, such as sugars, vitamins or prebiotics, if such elements are present in the original composition.

However, it is well understood that the composition according to the invention is capable of being used for purposes other than for feeding large animals. As a matter of fact, it is capable of serving to feed humans and any animal, in particular warm-blooded animals. It constitutes a food product or drug for human or veterinary use. The choice of a micro-organism or of a mixture of micro-organisms is determined by the end use of the composition according to the invention.

The method for preparing a food or medicinal composition according to the invention is characterised in that it comprises the steps of:
  dehydration of revivable micro-organisms; and
  mixing the dehydrated micro-organisms with particles at least 50% of which have a mean diameter greater than 250 µm.

Dehydration is carried out according to the conventional methods described above, and the mixing with particles at least 50% of which have a mean diameter greater than 250 µm is carried out according to common known techniques.

The method of preparation is preferably carried out under controlled moisture conditions ensuring a water activity lower than 0.3% in the composition obtained.

This invention will now be illustrated by means of the following examples.

Example 1

Particles containing vitamins A, D3, E, K, B1, B2, B3, B5, B6, B12 and C, folic acid, biotin, choline, lysine, methionine, tryptophan, citric acid, sodium carbonate and sodium bicarbonate, an absorbent and an emulsifier are prepared conventionally via rotogranulation. The particle size is adjusted so that said particles have a particle-size distribution of between 50 and 1,000 µm, 65% of said particles having a size greater than 250 µm. Next, 67% by weight of the total weight (w/w) of such particles are mechanically mixed with 33% w/w of a mixture of ferments containing the following micro-organisms: *Lactobacillus plantarum* and *Streptococcus infantarius*, titrating $2.52 \times 10^9$ CFU, marketed by the Lallemand™ Company under the trade name Adjulact™. The water activity of the effervescent composition A thus obtained according to the invention is 0.17.

Example 2

Particles, which contain Enerlyte™ (marketed by the Virbac™ Company) and citric acid, sodium carbonate and sodium bicarbonate, in order to create effervescence, are prepared conventionally via rotogranulation. The particle size is adjusted so that they have a particle-size distribution of between 50 and 1,000 µm, 54% of said particles having a size greater than 250 µm. Next, 67% w/w of such particles are mechanically mixed with 33% w/w of a mixture of ferments containing the following bacteria: *Lactobacillus plantarum, Streptococcus infantarius*, said mixture being titrated with $2.52 \times 10^9$ CFU (Adjulact™ by Lallemand™). An effervescent composition according to the invention is then obtained for which the mixture's water activity is 0.20.

Example 3

A tablet according to the invention is prepared, which contains $3 \times 10^9$ CFU of lyophilised *Saccharomyces cerevisiae*, having the formula:

| Constituents | Unit formula | Centesimal formula |
| --- | --- | --- |
| Lyophilised *Saccharomyces cerevisiae*\* | 499.94 mg | 35.71 |
| Mannitol | 689.22 mg | 49.23 |
| Crospovidone | 28.00 mg | 2 |
| Povidone | 56.00 mg | 4 |

-continued

| Constituents | Unit formula | Centesimal formula |
| --- | --- | --- |
| Microcrystalline cellulose | 126.00 mg | 9 |
| Magnesium stearate | 0.84 | 0.06 |
| TOTAL | 1400.00 mg | 100 |
| Wetting liquid: | Eliminated by drying after granulation | |
| Water | QS | |
| Ethanol | QS | |

\*Lyophilised *Saccharomyces cerevisiae* titrating $6 \times 10^9$ CFU/g

The mannitol, crospovidone, and microcrystalline cellulose are granulated with the hydroalcoholic solution of povidone. The granules thus obtained are dried and sized in order to obtain a granule size smaller than 800 micrometers. The size of 82% of the particles is larger than 250 micrometers.

The micro-organisms are homogenised in a ribbon blender together with the sized granules obtained.

Tableting is then carried out with a tablet-making machine equipped with dies and punches having a diameter of 17 mm; the walls of the dies and punches are pre-powdered with magnesium stearate, as a lubricant (the non-adhering excess quantity of magnesium stearate is suctioned up prior to tableting).

The compressive force is of the order of 10 to 16 kN, which makes it possible to obtain tablets preserving the structural integrity of the majority of the particles, which is estimated at more than 50%.

The amount of magnesium stearate distributed over the surface of a tablet is 0.84 mg or 0.6 for one thousand.

Example 4

A comparative study of the viability of the dehydrated bacteria *Lactobacillus plantarum* and *Streptococcus infantarius* present in various compositions was conducted under the following conditions.

The composition A according to the invention, described in Example 1, was apportioned per 25 g into welded aluminised pouches, which offer a very good gas and moisture barrier.

In addition, a composition B was prepared, which contains exactly the same bacteria and constituents of the particles as composition A, in the same quantities and proportions, but a large majority of the particles of which have a mean diameter smaller than 150 µm. Just as for composition A, this composition B, which is in the form of a powder, was apportioned per 25 g into welded aluminised pouches identical to those of composition A.

Finally, a composition C was prepared, which contains exactly the same bacteria and constituents of the particles as compositions A and B, according to the same method as that implemented in Example 1. However, in this case, the micro-organisms are constituent parts of the particles. The mean diameter of the particles of this composition C is larger than 300 µm. As in the preceding, this composition C was apportioned per 25 g into welded aluminised pouches identical to those of compositions A and B.

Then the various pouches of the compositions A, B and C were placed in an oven kept at a temperature of 40° C. and in the presence of 75% humidity. A pouch of each of the compositions was analysed each week with a view to determining the revivable bacteria content of each pouch. The results are reported in Table 1 below. They are expressed in CFU/g and in percentage of the initial concentration of revivable micro-organisms.

TABLE 1

| | Time | | | | | | |
|---|---|---|---|---|---|---|---|
| | 0 | 7 days | 14 days | 21 days | 28 days | 42 days | 50 days |
| Composition A | $4.18 \times 10^8$ (100%) | $3.71 \times 10^8$ (88.75%) | $3.05 \times 10^8$ (72.85%) | $2.12 \times 10^8$ (52.72%) | $1.10 \times 10^8$ (26.20%) | $1.10 \times 10^8$ (26.20%) | $1.10 \times 10^8$ (26.20%) |
| Composition B | $2.52 \times 10^8$ (100%) | $1.11 \times 10^8$ (43.94%) | $1.32 \times 10^8$ (52.18%) | $3.54 \times 10^7$ (14.04%) | $0.21 \times 10^7$ (0.8%) | — (0%) | — (0%) |
| Composition C | $2.94 \times 10^8$ (100%) | $0.15 \times 10^8$ (5%) | $0.32 \times 10^7$ (1%) | — (0%) | — (0%) | — (0%) | — (0%) |

It appears that the initial concentration of viable bacteria in composition A is higher than the initial concentration of viable bacteria in composition C, which is itself higher than the initial concentration of viable bacteria in composition B. Accordingly, it seems that the steps for preparing compositions B and C produced more significant stresses on the bacteria than the preparation steps for composition A.

For all compositions, the concentration of revivable bacteria decreases with relation to time. However, this concentration decreases more slowly in the case of composition A according to the invention than in the other compositions.

Furthermore, in the case of composition A, the concentration of revivable bacteria decreases until reaching a limit corresponding to approximately 26.20% of the 100% of revivable bacteria initially present in the pouches. As a result, the concentration of revivable bacteria appears to be stabilised over time, at least up to 50 days after being placed in pouches under the aforesaid operational conditions.

Of course, this stability observed under stressful conditions ought to be observed all the more so under actual conditions of storing the pouches at room temperature. Considering the fact that a week of storing the pouches under the operational conditions of this example is equal to approximately 3 months of storage at 25° C., it is permissible to conclude that a composition according to the invention, such as composition A, kept in pouches at temperatures of the order of 25° C., ought to contain a substantial quantity of revivable bacteria, in actual practice around 26.20% of the initial concentration, 18 months after being placed in pouches. At a minimum, this example demonstrates a sharply improved viability of the dehydrated micro-organisms in comparison with a composition that is substantially devoid of particles having a mean diameter and well below 250 µm (composition B), and in comparison with a composition in which the micro-organisms are constituent parts of the particles (composition C).

The invention claimed is:

1. A method of preparing a food or medicinal composition, wherein the method comprises:
   dehydrating uncoated, revivable micro-organisms, wherein the micro-organisms are a mixture of *Lactobacillus plantarum* and *Streptococcus infantarius*; and
   mixing the dehydrated uncoated, revivable micro-organisms with particles,
   wherein (i) each of said particles has a mean diameter, (ii) the mean diameters of said particles are distributed almost exclusively in a range of from 50 to 1,000 µm, (iii) about 65% of said particles have a mean diameter greater than 250 µm, and (iv) about 35% of said particles have a mean diameter of at most 250 µm,
   so as to form a composition comprising about 33% w/w revivable dehydrated micro-organisms, and further comprising about 67% w/w particles, wherein the micro-organisms are mixed with the particles in the composition,
   wherein the particles are granules comprising an aggregated and granulated mixture of (i) vitamins, trace elements, amino acids, sugars, and minerals or the salts thereof, and (ii) at least one carrier, and wherein the granules are substantially devoid of micro-organisms,
   wherein the composition has a water activity lower than 0.3, and
   wherein the micro-organisms in the composition have a revivability such that, after being kept moisture-free and at room temperature for 18 months, the composition comprises at least 20% revivable micro-organisms from amongst 100% revivable micro-organisms initially present in said composition.

2. The method of claim 1, being carried out under controlled moisture conditions ensuring a water activity lower than 0.2 in the composition obtained.

3. The method of claim 1, wherein the particles contain effervescent agents, wherein the effervescent agents comprise a mixture of at least one acid and one alkaline agent.

4. The method of claim 1, wherein the composition is soluble or dispersible in water.

5. The method of claim 1, wherein said composition in the form of capsules or tablets.

* * * * *